United States Patent [19]

Kedem et al.

[11] Patent Number: 5,097,982

[45] Date of Patent: Mar. 24, 1992

[54] PROGRAMMED MEDICATION DISPENSER APPARATUS

[76] Inventors: Dan Kedem, 43 Weizmann Street, Rehovot; Mordechai Ravid, 22 Arnon Street, Tel-Aviv, both of Israel

[21] Appl. No.: 141,493

[22] Filed: Jan. 7, 1988

[51] Int. Cl.[5] .................................. G07F 11/00
[52] U.S. Cl. ........................... 221/3; 221/8; 221/15; 221/94; 221/126; 221/129; 221/131; 221/133; 221/281
[58] Field of Search .............. 221/2, 3, 8, 15, 93, 221/94, 124, 133, 126, 129, 131, 281; 141/331

[56] References Cited

U.S. PATENT DOCUMENTS

| | | | |
|---|---|---|---|
| 3,315,840 | 5/1967 | Tollkuhn | 221/185 X |
| 3,556,342 | 1/1971 | Guarr | 221/2 |
| 4,017,001 | 4/1977 | Barthalon et al. | 221/129 X |
| 4,271,877 | 6/1981 | Whitaker et al. | 141/331 X |
| 4,695,954 | 9/1987 | Rose et al. | 221/3 X |
| 4,748,600 | 5/1988 | Urquhart | 221/15 X |
| 4,763,810 | 8/1988 | Christiansen | 221/15 X |

Primary Examiner—Michael S. Huppert
Assistant Examiner—Kenneth DeRosa
Attorney, Agent, or Firm—Benjmain J. Barish

[57] ABSTRACT

Medication dispenser apparatus comprises a plurality of containers for holding different kinds of medications; an injector for selectively injecting medications from their responsive containers; a dispensing station for receiving the ejected medications; and a programmable control for controlling the ejection of medications from their respective containers according to pre-programmed kinds of medication, amounts, and times. The described preferred embodiment is a group dispenser for dispensing medications for a plurality of patients, such as in the ward of a hospital, at predetermined times and in predetermined amounts.

6 Claims, 5 Drawing Sheets

PROGRAMMED MEDICATION DISPENSER APPARATUS

BACKGROUND OF THE INVENTION

The present invention relates to medication dispenser apparatus, and particularly to such apparatus which automatically dispenses the medication according to a predetermined programme. Two embodiments of the invention are described below for purposes of example: one embodiment is an individual dispenser for dispensing the medications for an individual patient; whereas the second embodiment is a group dispenser for dispensing the medications for a plurality of persons, such as in a hospital ward.

For maximum effectiveness, medications, such as pills, tablets and capsules, prescribed by physicians should be taken at the times and in the quantities prescribed. However, with the large number of medications some persons have to take, persons frequently forget to take certain medications at a prescribed time, and as a result may skip a dose, or take the dose too close to the time when the next dose is to be taken. This not only substantially reduces the effectiveness of the medication, but is also wasteful of expensive medications and may also be harmful to the patient.

Further, when medications are given to groups of patients, such as in a hospital ward, the medications prescribed by the physician for the individual patients are usually recorded by the nurses, subsequently obtained from the dispensary, and then distributed at preselected times of the day to all the patients. These are all very time-consuming operations for the nurses who are usually extremely busy with many other tasks. Moreover, such operations are prone to human error. In addition, there is no effective way to check what medication a patient actually received, in case an error occurred in filling a prescription for example.

An object of the present invention is to provide medications dispenser apparatus having advantages in the above respects.

BRIEF SUMMARY OF THE INVENTION

According to the present invention, there is provided a medication dispenser apparatus, comprising: a plurality of containers for holding different kinds of medications; ejector means for selectively ejecting medications from their respective containers; a dispensing station for receiving the ejected medications; and programmable control means for automatically controlling the ejection of medications from their respective containers according to pre-programmed kinds of medication, amounts, and times.

Two embodiments of the invention are described below for purposes of example.

One embodiment is an individual dispenser, for dispensing the medications for an individual patient. In this embodiment, the ejector means comprises an ejector at the dispensing station, and the plurality of containers are carried by an indexable member which is controlled by the programmable control means to selectively index the containers to the ejector at the dispensing station. A signalling device is provided controlled by the programmable control means to produce a signal upon the arrival of each predetermined time that medication is to be taken. This embodiment further includes a cover covering the containers, and a lock locking the cover to prevent access to the containers except by an authorized person. Also provided are a medication collector, and removing means at the dispensing station for removing therefrom any medication not removed within a predetermined time interval after having been dispensed thereto, and for transferring the unremoved medication to the medication collector.

The individual dispenser embodiment would be filled with the prescribed medication for a particular period of time, e.g., a week, and would be programmed to dispense the appropriate kind of medication and amount at the prescribed times. Such an apparatus would thus prevent a patient from taking medication at the wrong time, or at too closely spaced intervals. Where a medication is not taken within a predetermined interval of the prescribed time, the medication is automatically removed to a medication collector inaccessible to the patient thereby preventing the patient from taking the medication at an improper time, and also saving such medication which might otherwise go to waste. In addition, a record may be kept of each time the medication is not removed by the patient.

The second embodiment of the invention described below is in the form of a group dispenser, for dispensing medications to a group of patients, such as in a hospital ward. In this described embodiment, the plurality of containers are mounted in fixed positions, and the ejector means is located on one side of the containers. The apparatus further includes conveyor means located on the other side of the containers for receiving medications ejected therefrom by the ejector means and for conveying the medications laterally to the dispensing station.

The programmable control means in the group dispenser would include a computer and a keyboard for inputting the information prescribed by the physician identifying each patient and specifying the kind, quantity and time the medication is to be given to each patient. The apparatus preferably would be embodied in a portable form, such as on a wheeled cart, to enable the nurse to wheel the apparatus into each ward, and there to identify the ward via the keyboard. The computer would then sequentially display the name of each patient in the ward and the medication to be received by such patient at that time; and upon instruction from the attendant via the keyboard, would automatically dispense the appropriate kind and quantity of medications to be taken by such patient at the respective time.

The group dispenser thus saves considerable nurses' time in recording, sorting out, and distributing the medications to the various patients. It also reduces the possibility of error, since a validity check may be made by comparing the prescription for the respective patient recorded in the computer under the physician's instructions, with the medications actually dispensed for the respective patient. Moreover, a record may be retained in the computer as to the medications actually dispensed to each patient, which record could serve as a follow-up check by the physician to make sure that no error has occurred, as well as for other record purposes.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF TWO PREFERRED EMBODIMENTS

Figure 1:
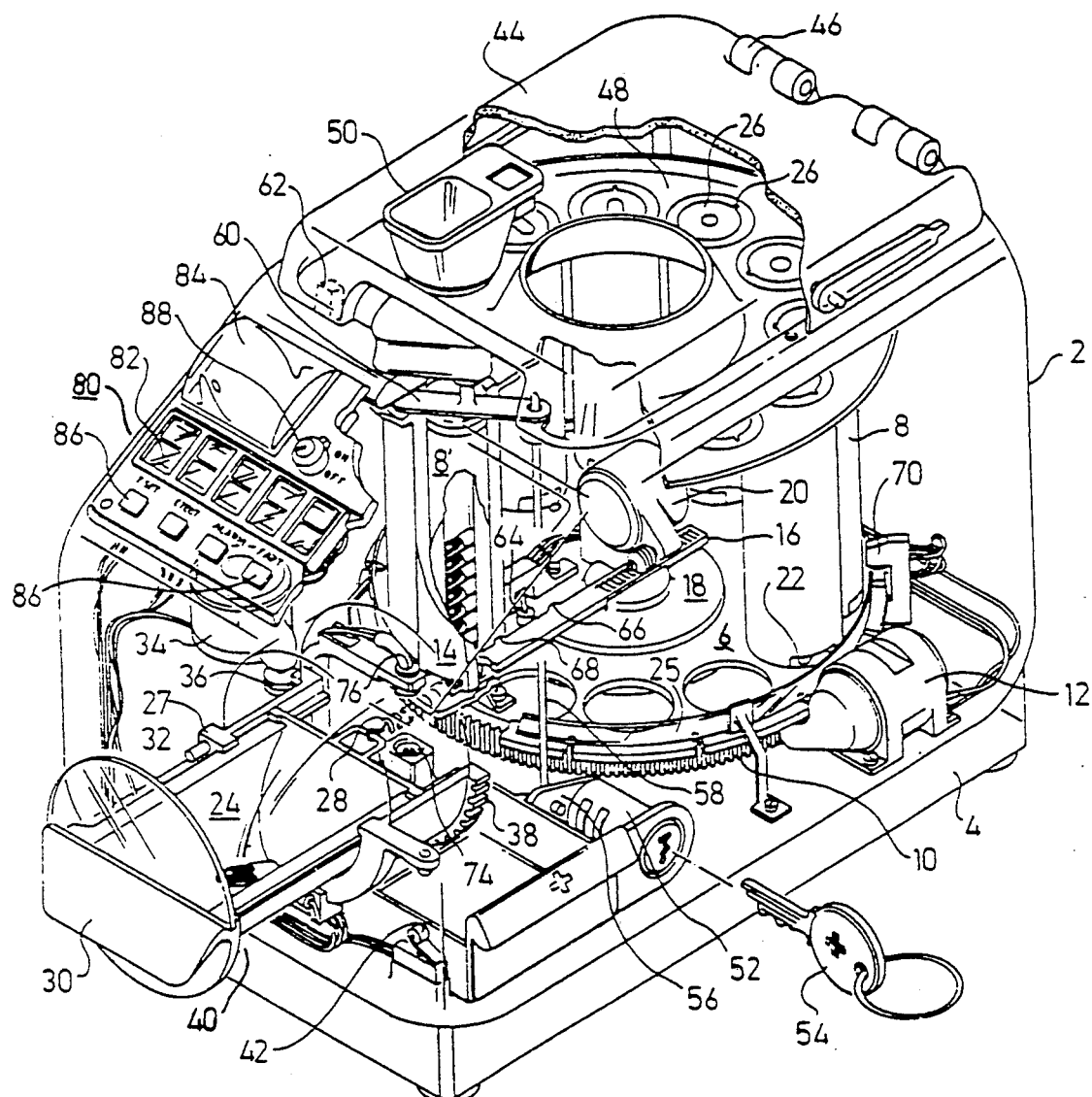
FIG. 1 illustrates one form of medication dispenser apparatus constructed in accordance with the invention particularly useful for dispensing medications for a single patient.
Figure 2:
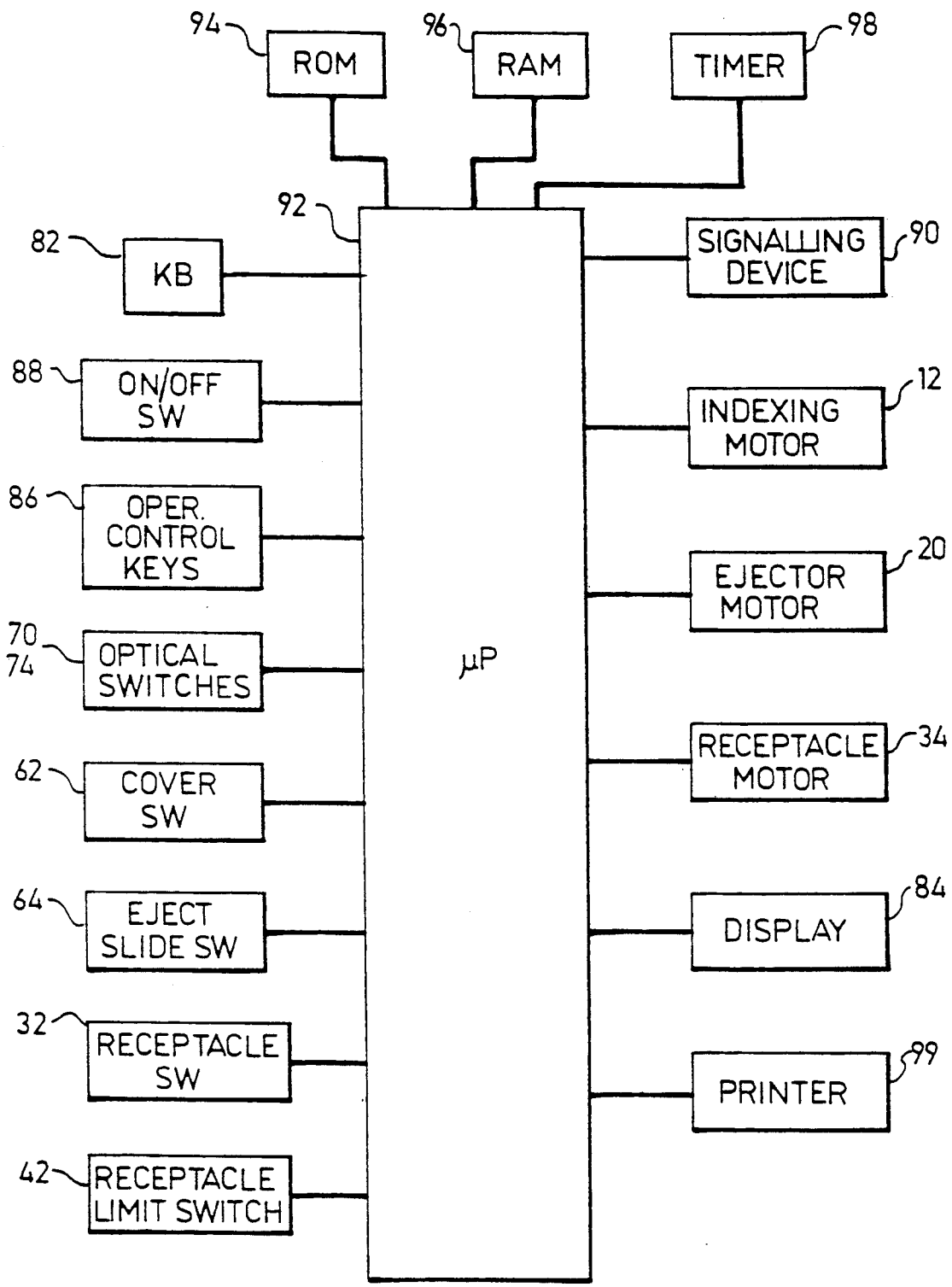
FIG. 2 is a block diagram illustrating the control system of the individual dispenser of FIG. 1.

The Individual Dispenser Embodiment (FIGS. 1 and 2)

The individual medication dispenser illustrated in FIGS. 1 and 2 is designed for use by a single patient. It would be filled at periodic intervals, such as once a week, and would then automatically dispense the prescribed kind of medication, and number of medications, at the prescribed times, all as pre-programmed in the apparatus.

Briefly, as each specified time arrives, or preferably a short interval before the prescribed time, the prescribed kind and number of medications is automatically dispensed into a receptacle, and at the specified time a signal is actuated to remind the patient to take the dispensed medications. If the patient does not actually take the medications within a predetermined time interval after the specified time, the dispensed medications are automatically removed into another receptacle so that such medications are no longer accessible to the patient, but are available for future use. This prevents the possibility of the patient taking the medications at too closely-spaced intervals. It also reduces wastage of such medications, and maintains a record of the medications not taken by the patient at the prescribed time.

More particularly, the dispensing apparatus illustrated in FIG. 1 comprises a housing, generally designated 2, including a base 4 on which is rotatably mounted a turntable 6 carrying a plurality of containers 8. One or more containers are provided for each of the medications to be taken by the patient. Turntable 6 is formed with gear teeth 10 around its outer edge meshable with a gear (not shown) rotated by a motor 12 fixed on base 4. Motor 12 thus rotates turntable 6 to selectively index the containers 8 to a dispensing station 14, shown in FIG. 1 as occupied by container 8'.

An ejector slide 16 is located on a platform 18 fixed to base 4 and is actuated by electric motor 20 to eject a single medication from the container 8' in the dispensing station 14 with each operation of the ejector. For this purpose, the lower end of each container 8 is formed with a slot 22 slightly larger than the thickness of the medications within the containers such that each operation of ejector slide 16 pushes the lowermost medication through its slot 22 into a receptacle 24 at the dispensing station 14. The opposite side of each container is formed with another slot (not shown) slightly smaller than the thickness of the medications within the container only to accommodate that end of the ejector slide. A guard 25 prevents the medications from leaving their containers except at the dispensing station 14.

Each of the containers 8 is prefilled with a number of the medications to be taken by the patient. Such medications may be in the form of pills, tablets, capsules, or the like. They can be prefilled in a holder 26 provided in each container 8 and dimensioned according to the particular size and shape of the respective medication. The medications are held in the holder 26 in the form of a vertical stack, such that with each operation of the ejector slide 16, the lowermost medication in the container (8') at the dispensing station 14 is ejected through its slot 22 into the receptacle 24. Preferably, each holder 26 is formed with a longitudinal rib 26' received within a longitudinal recess in the container 8 to assure the holder is properly oriented in the container.

The medication receptacle 24 is slidable within a holder 27 and is urged to a retracted position within the apparatus by a spring 28. The front side of the receptacle 24 is provided with a handle 30 which is graspable by the user in order to withdraw the receptacle from the apparatus in order to remove the medications received within it. The withdrawal of receptacle 30 for this purpose is sensed by a switch 32 carried by the holder 27.

Failure of the patient to withdraw receptacle 30, in order to remove the medications therein at a prescribed time, automatically actuates an electric motor 34. Motor 34 drives a gear 36 meshing with gear teeth 38 formed on the outer edge of holder 27 to rotate the holder, and thereby also the receptacle 24, to dump the medications within it into an underlying medication collector 40. As soon as motor 34 has rotated holder 27 and receptacle 24 to dump the medications into collector 40, as sensed by a limit switch 42, motor 34 is driven in the reverse direction to restore the holder 27 and the receptacle 24 to the normal position of the receptacle, as illustrated in FIG. 1, for receiving further medications during the next operation of the ejector slide 16.

The top of housing 2 is closed by a cover 44 pivotally mounted at one end by hinges 46. In FIG. 1, cover 44 is shown in its closed position but is broken-away to show the internal structure. An annular plate 48 is mounted to the upper ends of the containers 8 and supports a funnel 50 which may be slid along the plate in order to become aligned with the upper end of any one of the containers, to facilitate filling the containers with their respective medications.

Cover 44 may be locked in its closed position, preventing access to the upper ends of containers 8, by a cylinder lock 52 and a key 54 in order to prevent access to the containers 8 except to an authorized person having the proper key 54. Operation of the proper key 54 rotates a lever arm 56 connected by a rod 58 to a locking arm 60 to pivot the locking arm 60 either to a locking or to a released position with respect to cover 44. A switch 62 at the upper end of housing 2 is engageable by cover 44 when the cover is closed, to thereby indicate this closed condition of the cover. As will be described below, the apparatus is disabled whenever the cover is not in its closed position.

The illustrated apparatus includes a number of other switches to detect various conditions of the apparatus. Thus, it includes a switch 64 engageable by a lug 66 on ejector slide 16 actuated at the end of the forward stroke, and a second lug 68 actuated at the end of the return stroke. Switch 64 also detects the number of actuations of the ejector slide 16, and thereby the number of medications ejected.

The apparatus further includes an optical switch 70 cooperable with a light source (not shown) and with projections 72 formed in the outer edge of turntable 6, one for each of its containers 8, to detect the number of positions of movement of the turntable to bring a selected container 8 to the dispensing station 14, thereby detecting the medication dispensed during any particular operation of the apparatus. The apparatus includes a further optical switch 74 cooperable with a light source 76 at the dispensing station 14 for detecting the number of medications dispensed to receptacle 24.

In the apparatus illustrated in FIG. 1 includes a programmable control device is used for pre-programming the kind of medication, the number, and the time at which such medications are to be dispensed. For this purpose, the apparatus includes a computer, generally designated 80, having a keyboard 82 for programming the computer, and a display 84 for displaying any desired information, such as the programme of the medications to be dispensed, as well as the identification and number of medications actually dispensed. Keyboard 82 further includes a number of functional control keys, generally designed 86, as may be desired for any particular application, and an On/Off switch 88.

The illustrated apparatus further includes a signalling device, generally designated 90 (in FIG. 2), controlled by the computer to produce a signal, preferably an audible signal, upon the arrival of a pre-programmed time for dispensing a medication.

FIG. 2 is a block diagram illustrating the computer, generally designated 80, all the above-mentioned inputs to the computer, and also the outputs from the computer for controlling the above-mentioned devices.

Thus, the computer illustrated in FIG. 2 comprises a microprocessor 92 having a ROM (read only memory) 94 for storing the programme, and a RAM (random access memory) 96 for recording the inputted information. It also includes a timer 98 in the form of a real-time clock controlling the various operations. It may further include a printer 99 for producing printed records of the medications programmed as well as those actually dispensed.

As further shown in FIG. 2, the microprocessor 92 includes the following above-described devices as its inputs: keyboard 82, On/Off switch 88, operation control keys 86, optical switch 70 which identifies the container 8 from which medications were actually dispensed, optical switch 74 which identifies the number of medications actually dispensed, cover switch 62, ejector slide switch 64, receptacle switch 32 and receptacle limit switch 42. Microprocessor 92 produces outputs controlling the above-described devices, as follows: signalling device 90, indexing motor 12, ejector motor 20, receptacle motor 34, display 84, and optionally a printer 99.

The medication dispenser illustrated in FIGS. 1 and 2 operates as follows:

Keyboard 82 and the operation control keys 86 are used for inputting the programmed information concerning the time at which medications are to be taken, as well as the kind and quantity of such medications to be taken at that time. This information may be programmed for a predetermined period of time, such as for a week, and the information is stored in RAM 96.

Before or after the computer is so programmed, the various receptacles 8 of the dispenser apparatus are filled with the medications, by lifting cover 44 and using funnel 50 for this purpose. Cover 44 is then closed and locked by key 54 and cylinder lock 52, thereby preventing access to the medications except by an authorized person having the proper key. The closing of cover 44 is sensed by cover switch 62.

On/Off switch 88 is then actuated to place the apparatus in operation, during which timer 98 measures time in a real-time manner and controls the various operations, as follows:

At a predetermined time interval, e.g., 30 minutes, before a programmed time, indexing motor 12 is operated, under the control of optical switch 70, to index turntable 6 the required number of increments in order to bring the container 8 for the prescribed medication to the dispensing station 14. Ejector motor 20 is then operated, under the control of ejector slide switch 64, to drive ejector slide 16 one reciprocatory cycle in order to eject one of the medications (e.g., a pill, tablet or capsule) through the bottom slot 22 of the container in the dispensing station 14. If more than one such medication had been prescribed for that time, ejector slide 16 will be operated the required number of times to eject the prescribed number of medications. The ejected medications are received within receptacle 24 at the dispensing station 14.

If a second medication was prescribed at the specified time, indexing motor 12 is again operated to index turntable 6 in the same direction in order to bring the container 8 for the second prescribed medication to dispensing station 14, whereupon ejector motor 20 is again operated the required number of times to eject the specified number of medications into receptacle 24. In this manner, the turntable is rotated a complete revolution for each cycle, bringing to the dispensing station 14 each container 8 containing a prescribed medication(s), which medication(s) is (are) ejected into receptacle 24, the turntable stopping at the end of the cycle at its home position, preparatory to the next cycle.

It will be thus be seen that, at a predetermined time before the specified time for taking the medications, the required medications will have been dispensed into receptacle 24

When the specified time for taking the medications arrives, signalling device 90 is actuated to produce an audio signal and/or a visual signal (e.g., a blinking lamp) to inform the user that the time for taking the medications has arrived. The user should then grasp handle 30 to pull out receptacle 24 and remove the medications within the receptacle. This withdrawal of the receptacle 24 is sensed by receptacle switch 32.

If, after another predetermined time interval, e.g., another 90 minutes, receptacle 24 has not been withdrawn, as sensed by receptacle switch 32, receptacle motor 34 is energized. This rotates holder 26, and thereby receptacle 24, 180° in order to dump the contents of receptacle 24 into collector 40, whereupon receptacle limit switch 42 is energized to return holder 26 and receptacle 24 to their upright positions as illustrated in FIG. 1.

It will thus be seen that the prescribed medications are dispensed into receptacle 24 a predetermined time interval, e.g., 30 minutes, before the programme time in order to make the medications available to the user should it be more convenient for the user to take the medications earlier than the prescribed time. At the prescribed time, the signal is energized to alert the user to take the medications if not yet taken, and if the user does not take it within another predetermined time interval. e.g., 90 minutes, the medications within the receptacle 24 are dumped into collector 40 so that they are no longer available to the user. This precludes the user from taking the medications at too closely spaced intervals. At the same time it makes the non-used medications available for future use thereby preventing wastage. Further, a record is maintained (under the control of the non-actuated receptacle switch 32) of the times in which the prescribed medication was skipped.

The computer for programming the information and for controlling the various devices as described above may be one of the simpler, commercially-available computers, such as one including a single-chip microprocessor; and it may be programmed to perform the above-described operations using routine programming techniques. Accordingly, further details of the computer or the programme are not set forth herein.

Figure 3:
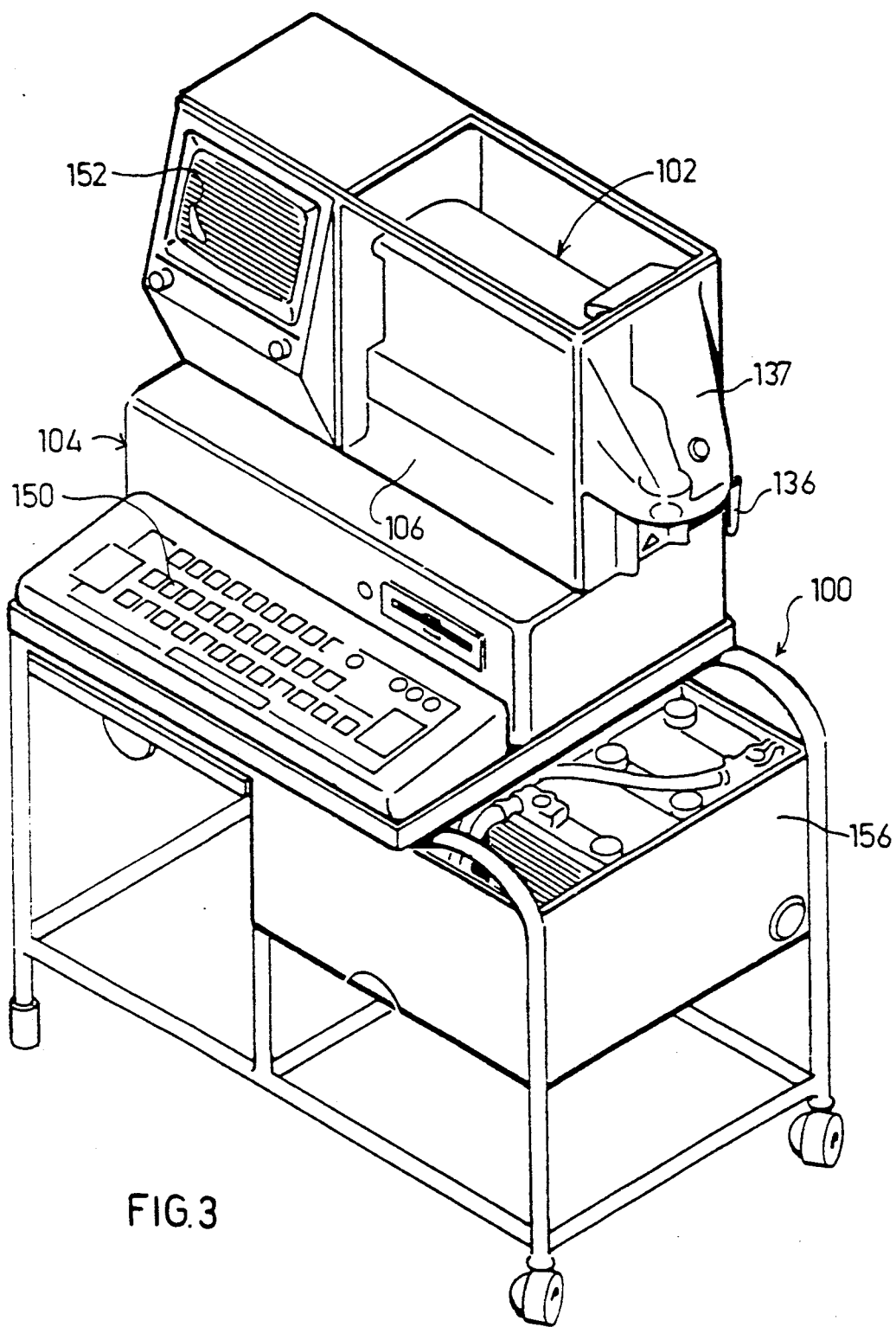
FIG. 3 illustrates another form of medication dispenser apparatus constructed in accordance with the present invention, particularly useful for dispensing medications to a group of patients, such as in a hospital ward.
Figure 4:
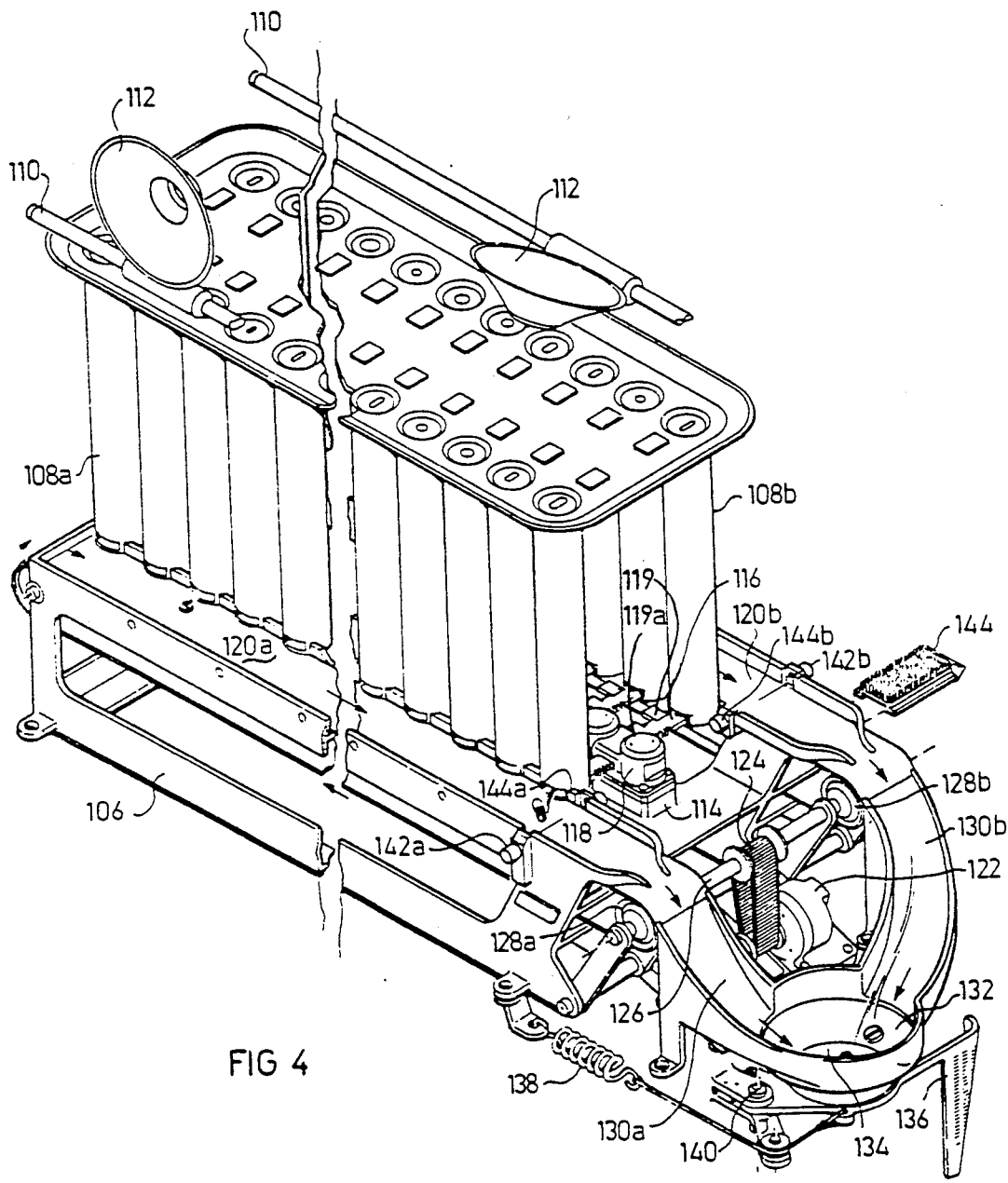
FIG. 4 illustrates the dispenser portion of the apparatus of FIG. 3.
Figure 5:
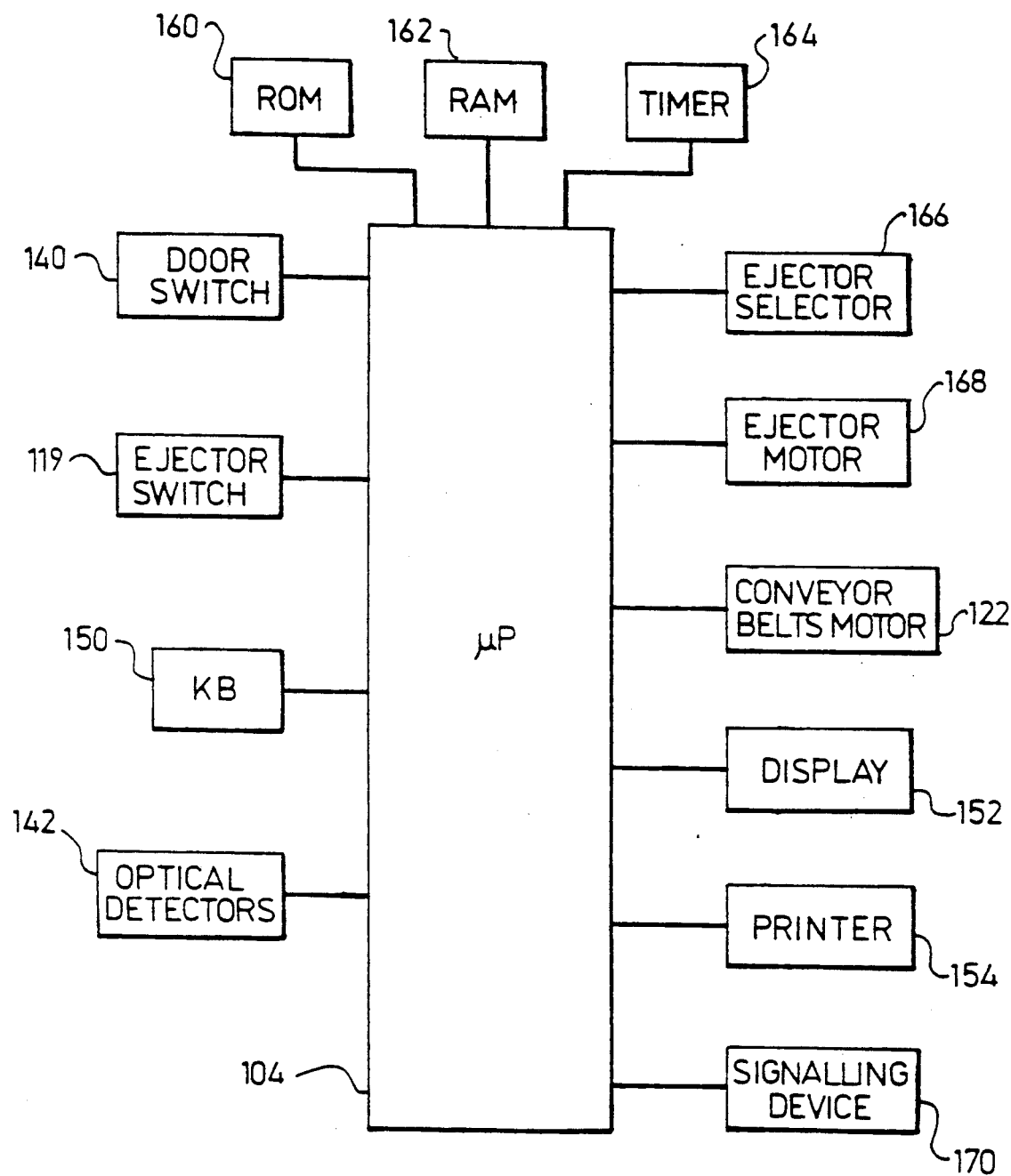
FIG. 5 is a block diagram illustrating the control system of the group medication dispenser of FIGS. 3 and 4.

The Group Dispenser Embodiment (FIGS. 3, 4 and 5)

The group medication dispenser illustrated in FIGS. 3, 4 and 5 is designed for dispensing medications for a group of users, such as patients in a ward of a hospital. FIG. 3 illustrates it as constructed in the form of a mobile unit, being supported on a wheeled cart 100. The medication dispenser, generally designated 102, is supported on the cart 100 together with a computer 104, so that both the dispenser and computer can be moved by a nurse into each ward in order to dispense the medications at one time for all the patients in the ward to receive medications at that time, according to the information pre-programmed in the computer.

The dispenser portion of the mobile apparatus illustrated in FIG. 3 is more particularly seen in FIG. 4. It includes a base 106 supporting a plurality of containers 108a, 108b each containing a supply of one of the medications to be dispensed. Since this apparatus is a group dispenser for dispensing medications for many patients, a large number of such containers are provided. These containers are fixedly mounted to base 106 in two spaced, parallel rows. A tube or track 110 is mounted above the upper open ends of each row of containers, and slidably receives a funnel 112 to facilitate filling the containers. Thus, each funnel 112 is slidable along its respective track 110, and is also pivoted thereon to selectively align the bottom of each funnel with the open end of the containers 108a, 108b.

A plurality of ejector mechanisms 114 are provided in the space between the two rows of containers 108a, 108b. Each ejector mechanism 114 includes an ejector slide 116 in alignment with one container of each row. Each ejector slide 116 is actuated by an ejector motor 118 to eject the bottom-most medication from the container in the respective row according to the direction of actuation of the slide. Thus, the medication to be dispensed is selected by the ejector slide actuated, and by the direction of actuation of such slide, and each actuation of the ejector slide dispenses one medication from the respective container. A switch 119 on each side of the ejector slide 116 and cooperable with a lug 119a on the respective side of the ejector slide identifies the ejector and direction actuated, and thereby the medication actually dispensed.

While the apparatus illustrated in FIG. 4 includes a plurality of fixed ejector mechanisms 114, one for each pair of containers 108a, 108b, it will be appreciated that a single ejector mechanism 114 could be supplied and moved along base 106 to align itself with the selected medication to be dispensed.

Base 106 further supports a pair of conveyor belts 120a, 120b, on the outboard sides of the two rows of containers 108a, 108b, to receive the medications dispensed from the containers by the operation of the ejector mechanisms 114 and to convey the medications laterally to the dispensing station. Conveyors belts 120a, 120b are closed loop belts driven by a motor 122 and a transmission including a coupling belt 124, a shaft 126, and a drum 128a, 128b for each of the conveyor belts. The two conveyor belts 120a, 120b terminate at the upper ends of a pair of slides 130a, 130b which convey by gravity the medications dispensed thereto to a receptacle 132 at the dispensing station.

Receptacle 132 includes a normally-closed bottom or door 134 so as to receive the dispensed medications. Bottom 134 may be pivoted by means of a hand lever 136 to permit the medications to fall by gravity from receptacle 132 into a container (not shown) normally held by the nurse underneath an outlet chute 137 (FIG. 3). The receptacle door 134 is normally urged by a spring 138 to its closed condition illustrated in FIG. 4 but is pivoted to its open condition by mechanism 139 when the nurse moves hand lever 136 to the side in order to receive the medications within receptacle 132. This operation of hand lever 136, to dispense the medications in receptacle 132, is sensed by a door switch 140.

Base 106 further includes an optical detector for detecting each medication dispensed by the conveyor belts to receptacle 132 at the dispensing station. Thus, conveyor belt 120a is provided with one optical detector in the form of a light source 142a and a light sensor 144a to detect each medication dispensed by that conveyor belt, and similarly conveyor belt 120b is provided with a light source 142b and a light sensor 144b to detect each medication dispensed by that conveyor belt. These optical detectors thus permit the apparatus to detect the number of medications actually dispensed during any particular operation of the apparatus. The kinds of medication dispensed are detected by the ejector switch 119 of the ejector mechanism 114 actuated. The apparatus can thus identify and maintain a record of the kinds of medications, as well as the number, actually dispensed during any particular operation.

The illustrated apparatus further includes a brush, shown at 144 in FIG. 4, disposed within base 106 in order to clean each conveyor belt 120a, 120b at the return stretch of the conveyor belt.

The computer 104 portion of the apparatus illustrated in FIG. 3 includes a keyboard 150 for manually inputting the data for each patient, a display 152 for displaying information, and a printer 154 (FIG. 5). In addition, the apparatus includes its own rechargeable battery power supply 156 mounted on cart 100 to provide mobility to the apparatus.

FIG. 5 illustrates the control system for controlling the operation of the apparatus of FIGS. 3 and 4. Thus, the computer 104 includes a ROM 160 for storing its programme, a RAM 162 for storing the inputted data, and a real-time clock timer 164.

The inputs into the computer 104 include keyboard 150 for inputting data, the optical detectors 142 for identifying the number of medications actually dispensed, the ejector switches 119 for identifying the kinds of medications actually dispensed, and the door switch 140 for identifying the time when the dispensing operation has been completed, and when the apparatus is thus ready for the next dispensing operation.

The outputs from computer 104 include an ejector selector circuit 166 which selects the ejector mechanism 114 to be actuated, and thereby selects the kind of medication to be dispensed, and also an ejector motor circuit 168 for controlling the selected ejector motor 118. The computer 104 further controls the conveyor belt motor 122, the display 152, the previously-mentioned printer 154, and a signalling device 170.

The dispensing apparatus illustrated in FIGS. 3-5 may be used in the following manner:

In each ward, the physician prescribes the required medication for each patient in that ward namely, the kind and quantity of the medication, and the time at which it is to be taken by the respective patient. This information is at that time, or subsequently, entered into the computer via keyboard 150. The computer thus retains in its memory 162 all the information concerning the medications to be taken by each patient in each ward. This information may also be printed out in printer 154 whenever desired.

At the prescribed times, the nurse wheels the apparatus into each ward and enters the identification of the ward into the computer via keyboard 150. The computer then automatically displays the names of the patients in that ward and the medications (both kind and quantity) prescribed for each patient. This information can be visually checked by the nurse, and assuming it appears in order, the nurse operates an appropriate key on the keyboard 150 for the respective patient.

The computer then controls the ejector mechanisms 114, as well as the conveyor belts 120a, 120b, to dispense the medication and quantity prescribed for the respective patient at the respective time. These medications are dispensed from containers 108a, 108b onto the conveyor belts 120a, 120b, which convey the medications via slides 130a, 130b to receptacle 132 at the dispensing station. The nurse then places a container under receptacle 132 and pivots lever 136 to open door 136 to permit the medications to fall via chute 137 into the container for the respective patient.

It will be seen that the quantity of medications actually dispensed is detected by optical detectors 142, and the kind of medication actually dispensed is detected by ejector switches 119. This information can be compared with the prescriptions stored in the computer to make sure no error occurred before the medication is actually handed to the patient. In addition, the information can be stored and printed out by printer 154. In this manner, a check is made to assure the patient is receiving actually what was prescribed, a record is maintained of the medications taken by the patient over any desired period of time, and the physician can subsequently check to see what medications were actually dispensed to the patient.

While the invention has been described with respect to two preferred embodiments, it will be appreciated that many other variations, modifications and applications of the invention may be made.

What is claimed is:

1. A medication dispenser apparatus, comprising: a plurality of containers fixedly mounted in a vertical position on a supporting base for holding different kinds of medications; ejector means located on said base at one side of said containers for selectively ejecting medications from their respective containers; a dispensing station for receiving the ejected medications; a track fixed over the upper ends of said plurality of containers; and a funnel pivotally mounted to, and movable along, said track into alignment with the upper ends of said containers to facilitate refilling them with their respective medications.

2. A medication dispenser apparatus, comprising:
a plurality of containers fixedly mounted on a supporting base for holding different kinds of medications;
ejector means located on said base at one side of said containers for selectively ejecting medications from their respective containers;
a dispensing station located laterally of said containers for receiving the ejected medications;
programmable control means for controlling the ejection of medications from their respective containers according to pre-programmed kinds of medication, amounts, and times;
and conveyor means including a conveyor belt located on the other side of said containers for receiving medications ejected therefrom by said ejector means and for conveying the medications laterally to said dispensing station;
said containers being arranged in two spaced, parallel rows, with said ejector means located in the space between the two rows so as to be accessible to the inner sides of the two rows of containers, there being conveyor means including a conveyor belt located along the outer side of each of the two rows of containers.

3. The apparatus according to claim 2, wherein said ejector means includes a plurality of ejectors each aligned with at least one of said containers.

4. The apparatus according to claim 2, wherein said conveyor means further includes a slide leading from an end of the conveyor belt to said dispensing station.

5. A medication dispenser apparatus, comprising:
a plurality of containers fixedly mounted on a supporting base for holding different kinds of medications;
ejector means located on said base at one side of said containers for selectively ejecting medications from their respective containers;
a dispensing station located laterally of said containers for receiving the ejected medications;
programmable control means for controlling the ejection of medications from their respective containers according to pre-programmed kinds of medication, amounts, and times;
conveyor means including a conveyor belt located on the other side of said containers for receiving medications ejected therefrom by said ejector means and for conveying the medications laterally to said dispensing station;
detector means for detecting the container from which medication was ejected and the number of medications conveyed to the dispensing station, during each operation of the apparatus;
and means for maintaining a record of the kind and number of medications dispensed for each patient;
said programmed control means comprising a computer including a keyboard for inputting information concerning the identity of each patient, the kind and quantity of medication to be dispensed for the respective patient, and the time at which the medication is to be dispensed for the respective patient.

6. The apparatus according to claim 5, further including a battery power supply, and a wheeled cart supporting said dispensing apparatus, including its computer, for moving same to different locations.

* * * * *